United States Patent
Wang et al.

(10) Patent No.: US 10,912,607 B2
(45) Date of Patent: *Feb. 9, 2021

(54) IRRIGATED ABLATION CATHETER SYSTEM WITH PULSATILE FLOW TO PREVENT THROMBUS

(71) Applicant: St. Jude Medical, Atrial Fibrillation Division, Inc., St. Paul, MN (US)

(72) Inventors: Huisun Wang, Maple Grove, MN (US); Jeremy D. Dando, Plymouth, MN (US); Hong Cao, Savage, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 876 days.

This patent is subject to a terminal disclaimer.

(21) Appl. No.: 15/489,608

(22) Filed: Apr. 17, 2017

(65) Prior Publication Data
US 2017/0273740 A1    Sep. 28, 2017

Related U.S. Application Data

(60) Continuation of application No. 14/204,598, filed on Mar. 11, 2014, now Pat. No. 9,622,814, which is a
(Continued)

(51) Int. Cl.
*A61B 18/14* (2006.01)
*A61B 18/00* (2006.01)

(52) U.S. Cl.
CPC . *A61B 18/1492* (2013.01); *A61B 2018/00011* (2013.01); *A61B 2018/00029* (2013.01);
(Continued)

(58) Field of Classification Search
CPC ...... A61B 18/1492; A61B 2018/00577; A61B 2018/00029; A61B 2018/00011; A61B 2218/002
See application file for complete search history.

(56) References Cited

U.S. PATENT DOCUMENTS 3,331,371 A    7/1967    Rocchi
3,671,979 A    6/1972    Moulopoulos
(Continued)

FOREIGN PATENT DOCUMENTS

WO    2005/048858    6/2005

OTHER PUBLICATIONS

Wittkampf, et al., "Saline-Irrigated Radiofrequency Ablation Electrode with External Cooling," Journal of Cardiovascular Electrophysiology, vol. 16, No. 3, Mar. 2005.
(Continued)

*Primary Examiner* — Jaymi E Della
(74) *Attorney, Agent, or Firm* — Dykema Gossett PLLC (57) ABSTRACT

The invention relates to an ablation catheter which controls the temperature and reduces the coagulation of biological fluids on an electrode of a catheter, prevents the impedance rise of tissue in contact with the electrode, and maximizes the potential energy transfer to the tissue, thereby allowing an increase in the lesion size produced by the ablation. The electrode includes passages positioned to allow saline flow out of an inner cavity of the electrode. This fluid flow is pulsatile to increase turbulence, reducing areas of stagnant flow, and produces a desired cooling effect.

22 Claims, 8 Drawing Sheets

Related U.S. Application Data division of application No. 11/646,275, filed on Dec. 28, 2006, now Pat. No. 8,690,870.

(52) U.S. Cl.
CPC ............... *A61B 2018/00577* (2013.01); *A61B 2218/002* (2013.01)

(56) References Cited

U.S. PATENT DOCUMENTS

| | | | |
|---|---|---|---|
| 4,084,606 A | 4/1978 | Mittleman | |
| 4,841,984 A | 6/1989 | Armeniades | |
| 4,857,054 A | 8/1989 | Helfer | |
| 5,056,517 A | 10/1991 | Fenici | |
| 5,092,844 A | 3/1992 | Schwartz et al. | |
| 5,112,301 A | 5/1992 | Fenton | |
| 5,207,645 A * | 5/1993 | Ross | A61M 5/14244 604/141 |
| 5,230,349 A | 7/1993 | Langberg | |
| 5,290,263 A * | 3/1994 | Wigness | A61M 25/0075 604/247 |
| 5,348,554 A | 9/1994 | Imran | |
| 5,403,276 A | 4/1995 | Schechter et al. | |
| 5,423,811 A | 6/1995 | Imran | |
| 5,427,114 A | 6/1995 | Colliver | |
| 5,462,521 A | 10/1995 | Brucker | |
| 5,545,161 A | 8/1996 | Imran | |
| 5,643,197 A | 7/1997 | Brucker | |
| 5,660,205 A | 8/1997 | Epstein | |
| 5,697,927 A | 12/1997 | Imran | |
| 5,792,140 A | 8/1998 | Tu | |
| 5,843,152 A | 12/1998 | Tu | |
| 5,913,856 A | 6/1999 | Chia | |
| 5,971,968 A | 10/1999 | Tu | |
| 6,017,338 A | 1/2000 | Brucker | |
| 6,044,845 A | 4/2000 | Lewis | |
| 6,602,242 B1 | 8/2003 | Fung | |
| 6,611,699 B2 * | 8/2003 | Messing | A61B 18/1492 600/372 |
| 6,659,959 B2 | 12/2003 | Brockway | |
| 6,955,675 B2 | 10/2005 | Jain | |
| 7,025,742 B2 | 4/2006 | Rubenstein | |
| 7,166,105 B2 | 1/2007 | Muller et al. | |
| 2002/0026188 A1 | 2/2002 | Babierz | |
| 2002/0058933 A1 | 5/2002 | Christopherson | |
| 2002/0120261 A1 | 8/2002 | Morris | |
| 2002/0177846 A1 | 11/2002 | Mulier et al. | |
| 2003/0014035 A1 | 1/2003 | Trombley et al. | |
| 2003/0069549 A1 | 4/2003 | MacMahon et al. | |
| 2003/0225364 A1 | 12/2003 | Kraft et al. | |
| 2004/0030279 A1 | 2/2004 | Rubenstein | |
| 2004/0098022 A1 | 5/2004 | Barone | |
| 2004/0102825 A1 | 5/2004 | Daoud | |
| 2004/0176801 A1 | 9/2004 | Edwards | |
| 2005/0049453 A1 | 3/2005 | Faulkner | |
| 2005/0070894 A1 * | 3/2005 | McClurken | A61B 18/1492 606/48 |
| 2005/0085769 A1 | 4/2005 | MacMahon et al. | |
| 2005/0137659 A1 * | 6/2005 | Garabedian | A61B 18/0206 607/96 |
| 2005/0143798 A1 | 6/2005 | Bleam et al. | |
| 2005/0149116 A1 | 7/2005 | Edwards et al. | |
| 2005/0209580 A1 | 9/2005 | Freyman | |
| 2005/0256521 A1 | 11/2005 | Kozel | |
| 2006/0036303 A1 | 2/2006 | Schwartz | |
| 2006/0058775 A1 | 3/2006 | Stevens et al. | |
| 2006/0058854 A1 | 3/2006 | Abrams et al. | |
| 2006/0229599 A1 | 10/2006 | Rashidi | |
| 2006/0278248 A1 | 12/2006 | Viswanathan | |
| 2007/0270791 A1 | 11/2007 | Wang | |
| 2008/0045943 A1 | 2/2008 | Wittkakmpf et al. | |

OTHER PUBLICATIONS

International Searching Authority; PCT/US2007/0088136; International Search Report dated May 13, 2008.

International Searching Authority; PCT/US2007/0088136; Written Opinion dated May 13, 2008.

Wittkampf, et al., "Radiofrequency Ablations With a Cooled Porous Electrode Catheter," JACC vol. 11, No. 2, Feb. 1988; 17A Abstracts.

"Medical Design with Sterile Piezo Motor Technology"; PI Medical. N.p . . . Web. Feb. 20, 2031 http://www.pi-medical.net/index.php.

"Piezoelectric Micropump" Takasago Fluid Systems. n.p., n.d. Web. Jun. 19, 2013 http://www.takasago-fluidics.com/products_pump/piezo/.

* cited by examiner

IRRIGATED ABLATION CATHETER SYSTEM WITH PULSATILE FLOW TO PREVENT THROMBUS

CROSS-REFERENCE TO RELATED APPLICATIONS

This application is a continuation of U.S. application Ser. No. 14/204,598, filed 11 Mar. 2014 (the '598 application), now U.S. Pat. No. 9,622,814, which is a division of U.S. application Ser. No. 11/646,275, filed 28 Dec. 2006 (the '275 application), now U.S. Pat. No. 8,690,870. This application is also related to U.S. application Ser. Nos. 11/646,237, 11/646,270, and 11/646,255, each filed 28 Dec. 2006 (the '237 application, the '270 application and the '255 application, respectively), now U.S. Pat. Nos. 7,824,406, 7,591,816 and 7,951,143, respectively. The '598 application, the '275 application, the '237 application, the '270 application and the '255 application are all hereby incorporated by reference as though fully set forth herein.

BACKGROUND OF THE INVENTION a. Field of the Invention

The instant invention relates to catheters. In particular, the instant invention relates to an irrigated ablative catheter system with pulsatile flow to prevent thrombus.

b. Background Art

Electrical stimulation of myocardial tissue controls the pumping action of the heart. Stimulation of this tissue in various regions of the heart is controlled by a series of conduction pathways contained within the myocardial tissue. In a healthy heart, contraction and relaxation of the heart muscle (myocardium) occur in an organized fashion as electro-chemical signals pass sequentially through the myocardium from the sinoatrial (SA) node, which consists of a bundle of unique cells disposed in the wall of the right atrium, to the atrioventricular (AV) node, and then into the left and right ventricles via a route that includes the His-Purkinje system. The AV node is located near the ostium of the coronary sinus in the interatrial septum in the right atrium. Each cell membrane of the SA node has a characteristic tendency of a gradual leak of sodium ions over time leading to a periodic break down of the cell membrane periodically, thus allowing an inflow of sodium ions, and thereby causing the SA node cells to depolarize. The SA node cells are in communication with the surrounding atrial muscle cells such that the depolarization of the SA node cells causes the adjacent atrial muscle cells to also depolarize. This depolarization results in atrial systole, during which the atria contract to empty and fill blood into the ventricles. The AV node detects the atrial depolarization from the SA node and, in turn, relays the depolarization impulse into the ventricles via the bundle of His and Purkinje fibers following a brief conduction delay. The His-Purkinje system begins at the AV node and follows along the membranous interatrial septum toward the tricuspid valve through the AV septum and into the membranous interventricular septum. At about the middle of the interventricular septum, the His-Purkinje system splits into right and left branches, which straddle the summit of the muscular part of the interventricular septum.

Abnormal rhythms generally referred to as arrhythmia can occur in the heart. Cardiac arrhythmias arise when the pattern of the heartbeat is changed by abnormal impulse initiation or conduction in the myocardial tissue. The term tachycardia is used to describe an excessively rapid heartbeat resulting from repetitive stimulation of the heart muscle. Such disturbances often arise from additional conduction pathways that are present within the heart either from a congenital developmental abnormality or an acquired abnormality, which changes the structure of the cardiac tissue, such as a myocardial infarction.

A common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Atrial arrhythmia may also occur. Three of the most common atrial arrhythmia are ectopic atrial tachycardia, atrial fibrillation, and atrial flutter. Atrial fibrillation can cause significant patient discomfort and even death because of a number of associated problems, including e.g., an irregular heart rate (which causes patient discomfort and anxiety), loss of synchronous atrioventricular contractions (which compromises cardiac hemodynamics, resulting in varying levels of congestive heart failure) and stasis of blood flow (which increases the likelihood of thromboembolism).

In the past, problems associated with arrhythmia have been treated with pharmacological treatment. Such treatment may not be effective in all patients and is frequently plagued with side effects, including, e.g., dizziness, nausea, vision problems, and other difficulties.

Alternatively, such disturbances are treated by identifying the conductive pathways and then severing part of this pathway by destroying these cells, which make up a portion of the pathway. Traditionally, this has been done by either cutting the pathway surgically; freezing the tissue, thus destroying the cellular membranes; or by heating the cells, thus denaturing the cellular proteins. The resulting destruction of the cells eliminates their electrical conductivity, thus destroying, or ablating, a certain portion of the pathway. By eliminating a portion of the pathway, the pathway may no longer maintain the ability to conduct, and the tachycardia ceases.

Catheters are a common medical tool that has been used for many years. They are employed, e.g., for medical procedures to examine, diagnose, and treat while positioned at a specific location within the body that is otherwise inaccessible without more invasive procedures. In such procedures, a catheter is first inserted into a vessel near the surface of the body and the guided to a specific location within the body. For example, a catheter may be used to convey an electrical stimulus to a selected location within the human body or a catheter with sensing electrodes may be used to monitor various forms of electrical activity in the human body.

Catheters have increasingly become a common medical procedure for the treatment of certain types of cardiac arrhythmia. Catheter ablation is based on the idea that by ablation (i.e., destroying) abnormal tissue areas in the heart, its electrical system can be repaired and the heart will return to a normal rhythm. During catheter ablation, the catheter is typically inserted in an artery or vein in the leg, neck, or arm of the patient and then threaded, sometimes with the aid of a guide wire or introducer, through the vessels until a distal tip of the catheter reaches the desired location for the medical procedure in the heart.

Most often, cardiac ablation is used to treat supraventricular tachycardias, or SVTs. Types of SVTs are atrial fibrillation, atrial flutter, AV nodal reentrant tachycardia, AV reentrant tachycardia, and atrial tachycardia. Less frequently, ablation can treat heart rhythm disorders that begin in the heart's lower chambers, known as the ventricles. The most common, ventricular tachycardia may also be the most dangerous type of arrhythmia because it can cause sudden cardiac death. For patients at risk for sudden cardiac death, ablation often is used along with an implantable cardioverter device (ICD). The ablation decreases the frequency of abnormal heart rhythms in the ventricles and therefore reduces the number of ICD shocks a patient may experience. For many types of arrhythmias, catheter ablation is successful in 90-98 percent of cases, thus eliminating the need for open-heart surgeries or long-term drug therapies.

During conventional catheter ablation procedures, an energy source is in contact with cardiac tissue to heat the tissue and create a permanent scar or lesion that is electrically inactive or non-contractile. These lesions are designed to interrupt existing conduction pathways commonly associated with arrhythmias within the heart. The particular area for ablation depends on the type of underlying arrhythmia. One common ablation procedure treats atrioventricular nodal reentrant tachycardia (AVNRT). The use of electrode catheters for ablating specific locations within the heart has also been disclosed in, e.g., U.S. Pat. Nos. 4,641,649, 5,228,442, 5,231,995, 5,263,493, and 5,281,217.

Many variations of ablations procedures are known. For example, ablation of fast or slow AV nodal pathways is disclosed in Singer et al., Catheter Ablation for Arrhythmias, Clinical Manual of Electrophysiology, 421-431 (1993).

Another medical procedure using ablation catheters with sheaths to ablate accessory pathways associated with W-P-W using both a transseptal and retrograde approach is discussed in Saul et al., Catheter Ablation of Accessory Atrioventricular Pathways in Young Patients: Use of long vascular sheaths, the transseptal approach and a retrograde left posterior parallel approach, *Journal of the American College of Cardiology,* 21(3), 571-583 (1993). Additional catheter ablation procedures are disclosed in Swartz, Radiofrequency Endocardial Catheter Ablation of Accessory Atrioventricular Pathway Atrial Insertion Sites, *Circulation,* 87 (2), 487-499 (1993).

Ablation of a specific target requires precise placement of the ablation catheter within the heart. Precise positioning of the ablation catheter is especially difficult due the physiology of the heart, particularly since the heart continues to beat throughout the ablation procedures. Typically, the choice of placement of the catheter is determined by a combination of electrophysiological guidance and fluoroscopy. Fluoroscopy is placement of the catheter in relation to known features of the heart, which are marked by radiopaque diagnostic catheters that are placed in or at known anatomical structures, such as the coronary sinus, high right atrium, and the right ventricle.

Ablation procedures using guiding introducers to direct an ablation catheter to a particular location in the heart for treatment of atrial arrhythmia have been disclosed in, e.g., U.S. Pat. Nos. 5,427,119, 5,497,774, 5,564,440, 5,575,766, 5,628,316, and 5,640,955. During these procedures, ablation lesions are produced in the heart.

A variety of energy sources can be used to supply the energy necessary to ablate cardiac tissue and create a permanent lesion. Such energy sources include direct current, laser, microwave, and ultrasound. Because of problems associated with the use of DC current, radiofrequency (RF) has become the preferred source of energy for ablation procedures. The use of RF energy for ablation has been disclosed, e.g., in U.S. Pat. Nos. 4,945,912, 5,242,441, 5,246,438, 5,281,213, 5,281,218, and 5,293,868. The use of RF energy with an ablation catheter contained within a transseptal sheath for the treatment of W-P-W in the left atrium is disclosed in Swartz et al., Radiofrequency Endocardial Catheter Ablation of Accessory Atrioventricular Pathway Atrial Insertion Sites, *Circulation,* 87: 487-499 (1993). See also Tracey, Radio Frequency Catheter Ablation of Ectopic Atrial Tachycardia Using Paced Activation Sequence Mapping, *J. Am. Coll. Cardiol.* 21: 910-917 (1993).

In addition to radiofrequency ablation catheters, thermal ablation catheters are also used. During thermal ablation, a heating element, secured to the distal end of a catheter, heats thermally conductive fluid. This fluid then contacts the human tissue to raise its temperature for a sufficient period of time to ablate the tissue. A method and device for thermal ablation using heat transfer is disclosed in U.S. Pat. No. 5,433,708. U.S. Pat. No. 5,505,730 discloses another thermal ablation procedure. This procedure utilizes a thermal electrode secured to a catheter and located within a balloon with openings in that balloon. The openings permit a heated conductive fluid introduced into the balloon from the catheter to escape to contact the tissue to be ablated.

Conventional ablation procedures use a single electrode secured to the tip of an ablation catheter. It has become increasingly more common to use multiple electrodes affixed to the catheter body. Such ablation catheters often contain a distal tip electrode and a plurality of ring electrodes as disclosed in, e.g., U.S. Pat. Nos. 4,892,102, 5,228,442, 5,327,905, 5,354,297, 5,487,385, and 5,582,609.

During conventional ablation procedures, the ablating energy is delivered directly to the cardiac tissue by an electrode on the catheter placed against the surface of the tissue to raise the temperature of the tissue to be ablated. The increase in tissue temperature also results in a rise in the temperature of blood surrounding the electrode. This rise in temperature often results in the formation of coagulum on the electrode, which in turn reduces the efficiency of the ablation electrode. Thus, to achieve efficient and effective ablation, coagulation of blood should be avoided. This coagulation problem can be especially significant when linear ablation lesions or tracks are produced because such linear ablation procedures take more time than ablation at only a single location.

The formation of linear lesions within a heart via conventional ablation tip electrode requires use of procedures such as e.g., a "drag burn." A "linear lesion" means an elongate, continuous lesion, which may be straight or curved, that blocks electrical conduction. During a "drag burn" procedure, while energy is supplied to the electrode, the electrode is drawn across the tissue to be ablated, producing a line of ablation. Alternatively, a series of points of ablation are formed in a line created by moving the tip electrode incremental distances across the cardiac tissue. The effectiveness of these procedures depends on a number of variables such as e.g., (i) the position and contact pressure of the tip electrode of the ablation catheter against the cardiac tissue, (ii) the time that the tip electrode of the ablation catheter is placed against the tissue, (iii) the amount of coagulum formed as a result of heat generated during the ablation procedure, and (iv) other variables associated with a beating heart, especially an erratically beating heart. An uninterrupted track of cardiac tissue needs to be ablated as unablated tissue or incompletely ablated tissue may remain electrically active, thereby permitting the continuation of stray circuits that cause arrhythmia.

More efficient ablation can be achieved if a linear lesion of cardiac tissue is formed during a single ablation procedure. The production of linear lesions in the heart by use of an ablation catheter is disclosed in, e.g., U.S. Pat. Nos. 5,487,385, 5,582,609, and 5,676,662. A specific series of linear lesions formed in the atria for the treatment of atrial arrhythmia are disclosed in U.S. Pat. No. 5,575,766.

Physical contact of the cardiac tissue with an electrode of the ablation catheter is typically used to perform these procedures on electrically inactive or non-contractile tissue. Conventional tip electrodes with adjacent ring electrodes cannot perform this type of procedure, however, due to the high amount of energy necessary to ablate sufficient tissue to produce a complete linear lesion. In addition, conventional ring electrode ablation may leave holes or gaps in a lesion, which can provide a doorway for the creation of unwanted circuits.

U.S. Pat. No. 5,334,193 discloses an ablation catheter for use in the heart that contains a pair of intertwined helical electrodes. The helically wound electrode is affixed to the surface of the catheter body over a distance of about eight centimeters from the distal tip of the catheter body. Other helical electrodes are disclosed in WO 95/10319 as well as U.S. Pat. Nos. 4,161,952, 4,776,334, 4,860,769, 4,934,049, 5,047,026, and 5,542,928.

As discussed a variety of energy such as radiofrequency (RF), microwave, ultrasound, and laser energy have been used for ablation. With RF energy, a catheter with a conductive inner core and a metallic tip are placed in contact with the myocardium and a circuit is completed with a patch placed on the patient's body behind the heart. The catheter is coupled to a RF generator such that application of electrical energy creates localized heating in the tissue adjacent to the distal (emitting) electrode. The peak tissue temperatures during catheter delivered application of RF energy to the myocardium occur close to the endocardial surface, such that the lesion size produced is limited by the thermodynamics of radiant heat spread from the tip. The amount of heating which occurs is dependent on the area of contact between the electrode, and the tissue and the impedance between the electrode and the tissue. The higher the impedance, the lower the amount of energy transferred into the tissue.

During RF catheter ablation, local temperature elevation can result in coagulum formation on the ablation electrode, resulting in impedance rise. As the impedance increases, more energy is passed through the portion of the tip without coagulation, creating even higher local temperatures and further increasing coagulum formation and the impedance. Finally, enough blood coagulates onto the tip that no energy passes into the tissue. The catheter must now be removed from the vascular system, the tip area cleaned and the catheter repositioned within the heart at the desired location. Not only can this process be time consuming, but also it may be difficult to return to the previous location because of the reduced electrical activity in the regions, which have previously been ablated. A recent study has also demonstrated the formation of a so-called soft thrombus during experimental ablations (Demonlin et al., Soft thrombus formation in radiofrequency catheter ablation, *Pacing clin. electrophysiol.* 25(8): 1219-1222 (2002)). The formation of the so-called soft thrombus results from heat induced protein denaturation and aggregation and occurs independent of heparin concentration in serum.

To prevent the occurrence of, e.g., soft thrombus, blood coagulation, and steam pop during ablation, the catheter may be cooled by passing a fluid through the catheter during ablation. Saline irrigation is an effective way to cool the ablation electrode and keep efficient flow around the electrode to prevent blood coagulation. Furthermore, the surface cooling that results from the saline irrigation reduces heating at the point of highest current density where excessive temperatures would normally produce charring, crater formation and impedence rises (Thomas et al., A comparison of open irrigated and non-irrigated tip catheter ablation for pulmonary vein isolation, *Europace* 6: 330-335 (2004)). Open irrigated ablation catheters are currently the most common irrigated catheters in the electrophysiology field. Examples of these devices include Thermocool® by Biosense Webster and Coolpath® by Irvine Biomedical.

In order to effectively cool the electrode at any possible catheter electrode orientation, it is important to maintain a saline flow rate of, for example, 20-30 ml/minute. The high saline volume can result in a deterioration of the patient's condition. In part, this occurs due to hemodilution affecting the volume, placing additional stresses on the heart/circulatory system. This can lead to edema and swelling. Thus, there is a need for a method of cooling the electrode during ablation without using an excess of saline in irrigation.

Another possible problem with open irrigated ablation catheters is that there are no physical blocks to prevent the backflow of blood when saline irrigation flow stops. There is a potential problem of blood's flowing back into the catheter through the irrigation orifices due to blood pressure inside the heart—especially inside the ventricle. This blood backflow could cause blood clotting inside the catheter, potentially resulting in catheter malfunction.

The current method of preventing backflow of blood into the catheter is maintaining a low irrigation flow rate at all times during a procedure. However, this method can result in delivery of an excess of saline to the patient's bloodstream over a long procedure. Fluid overload or hemodilution can cause many complications in heart patients. Thus, it is desirable to have a catheter which can prevent blood backflow into the catheter.

Figure 10A:
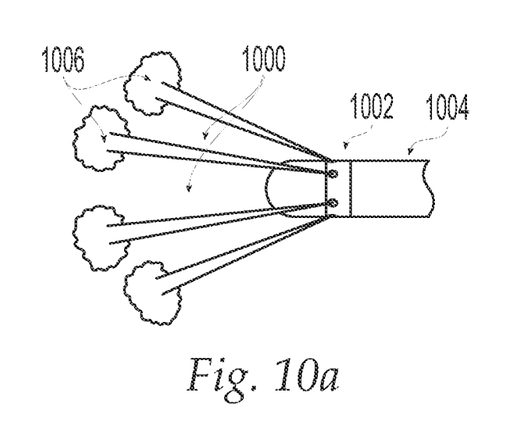
FIG. 10(a) is an illustration of steady state irrigation flow.
Figure 13A:
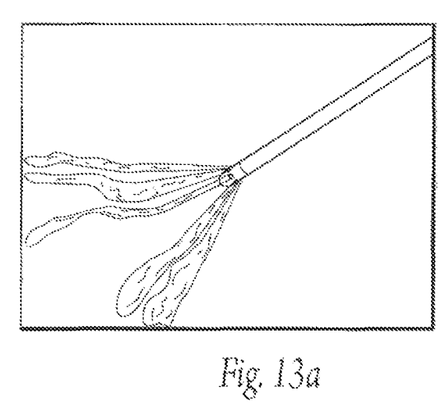
FIG. 13(a) is a photograph of steady state flow irrigation from an external irrigated catheter at horizontal orientation.
Figure 13B:
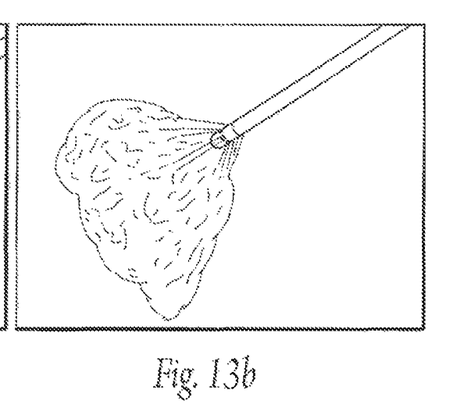
FIG. 13(b) is a photograph of pulsatile flow irrigation from an external irrigated catheter at horizontal orientation.
Figure 13C:
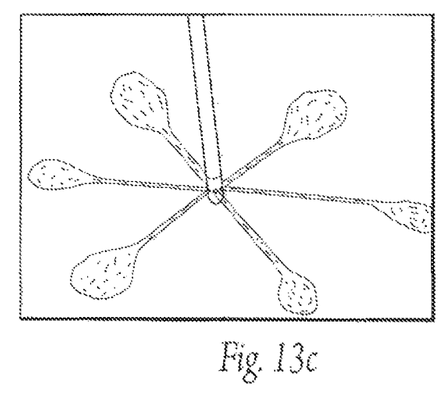
FIG. 13(c) is a photograph of steady state flow irrigation from an open irrigated catheter at vertical orientation.
Figure 13D:
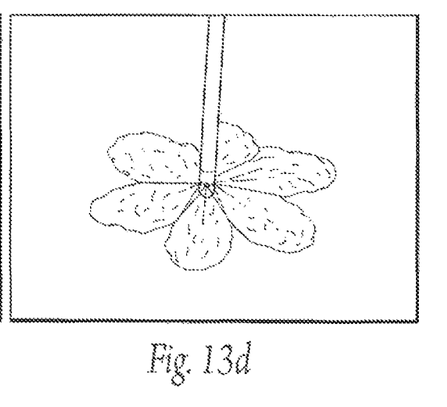
FIG. 13(d) is a photograph of pulsatile flow irrigation from an open irrigated catheter at vertical orientation.

Another issue for irrigated ablation catheters is stagnation areas around the electrode in which blood coagulation is more likely to occur. FIG. 10(*a*) shows the stagnation areas 1000 at the distal end of an electrode 1002 when a catheter 1004 contacts the tissue horizontally and saline flow 1006 is used for cooling. The stagnation areas can also be seen in FIG. 13(*a*), in which a steady state irrigation flow is shown by a dye used with the saline. The reason for the stagnation is that the saline flowing away from the electrode does not have enough time to develop turbulence to cover the distal area. There are a number of ways to increase flow turbulence. One way is to increase the saline flow rate. Again, as explained above, increased saline flow is detrimental to the patient. Thus, it is desirable to have method of increasing turbulence of saline flow around a catheter tip without increasing saline dosage to a patient.

SUMMARY OF THE INVENTION

It is desirable to be able to provide an improved ablation catheter system with pulsatile flow to prevent thrombus.

A first embodiment of the invention is an irrigated ablation catheter and a pump system generating pulsatile flow, wherein the irrigated ablation catheter comprises a distal electrode assembly, a shaft connected to the distal electrode assembly, and an interior portion leading to openings through which the pulsatile flow of a fluid is directed from the interior portion to an area outside the catheter.

In a variation of the first embodiment of the invention, the irrigated catheter may further comprise a valve movable between a first position to block fluid flow through the one or more openings and a second position to unblock fluid flow through the one or more openings. The valve may be moved between the first position and the second position in response to a variable pressure generated by the pump system in the interior portion of the irrigated ablation catheter.

The distal electrode assembly of the first embodiment of the invention may have external irrigation flow.

The distal electrode assembly of the first embodiment of the invention may have open irrigation flow.

The pump system of the first embodiment of the invention may comprise a positive displacement pump driven by a stepper motor.

The first embodiment of the invention may have a flow rate between 2 ml/minute and 20 ml/minute with a frequency of between 30 cycles per minute and 120 cycles per minute. The term "frequency" means the number of repetitions of a periodic process in a unit of time. The term "periodic" means occurring or recurring at regular intervals.

The pulsatile flow of the first embodiment of the invention may be generated by an on/off valve, a compliance chamber, and a positive displacement pump. The on/off valve and the compliance chamber may be located inside the shaft of the catheter. The on/off valve may be a push/pull type valve to cover and uncover the one or more openings to prevent and allow flow, respectively. The on/off valve may be a rotation type valve to cover and uncover the one or more openings to prevent and allow flow, respectively.

The first embodiment of the invention may also include an insulating element that provides thermal insulation between the fluid flow and the distal electrode assembly.

The first embodiment of the invention may also include a valve to prevent backflow of fluids into the catheter. The valve to prevent backflow may be umbrella-shaped, and collapsible and expandable to uncover and cover the one or more openings to allow and prevent flow, respectively. The valve to prevent backflow of fluids may comprise a balloon that is alternately inflated and deflated to prevent and allow flow, respectively. The valve to prevent backflow of fluids may have a spring-loaded valve element that may bear against a seal element when closed.

A second embodiment of the invention is a method of preventing thrombus formation during cardiac ablation comprising using an irrigated catheter with an interior portion leading to one or more openings through which pulsatile flow of a fluid is directed from within the catheter to an area outside the catheter.

The second embodiment of the invention may further comprise: blocking fluid flow between the interior portion of the catheter through the one or more openings and the area outside the catheter in a first time period; and allowing fluid flow from the interior portion of the catheter through the one or more openings to the area outside the catheter in a second time period. Blocking fluid flow may comprise moving a valve to a first position to block fluid flow through the one or more openings, and wherein allowing fluid flow comprises moving the valve to a second position to unblock fluid flow through the one or more openings. The valve may be moved between the first position and the second position in response to a variable pressure generated in the interior portion of the catheter.

An third embodiment of the invention is an irrigated ablation catheter comprising an electrode assembly having an inner cavity and a plurality of irrigation holes; an elongate shaft; a proximal handle; a fluid lumen having a distal end and a proximal end, the distal end connecting to the proximal handle; an on/off valve located inside of the proximal handle to control passage of a fluid; a volume compliance chamber having an expandable body, a distal end, and a proximal end, wherein the distal end of the volume compliance chamber connects to on/off valve and the proximal end of the volume compliance chamber connects to the fluid lumen, and the volume compliance chamber is located within the proximal handle.

The on/off valve of the third embodiment of the invention may be a solenoid actuated valve.

The on/off valve of the third embodiment of the invention may be controlled by an electronic circuit which allows variations in on and off durations and frequencies.

The on and off frequencies of the third embodiment of the invention are 50% and 50%.

The on and off frequencies of the third embodiment of the invention may be variable ranging from 30% to 70%.

The compliance chamber of the third embodiment of the invention is an elastic tube made of an elastic material such as polyurethane, silicone, or other elastic materials.

The foregoing and other aspects, features, details, utilities, and advantages of the present invention will be apparent from reading the following description and claims, and from reviewing the accompanying drawings.

DETAILED DESCRIPTION OF THE INVENTION

Several embodiments of an irrigated ablation catheter having a valve to prevent backflow are depicted in the figures. As described further below, the irrigated ablation catheter having a valve to prevent backflow according to the present invention provides a number of advantages, including, for example, reducing delivery of saline to a patient's bloodstream and reducing blood clotting inside the catheter.

Figures 1A, 1B:
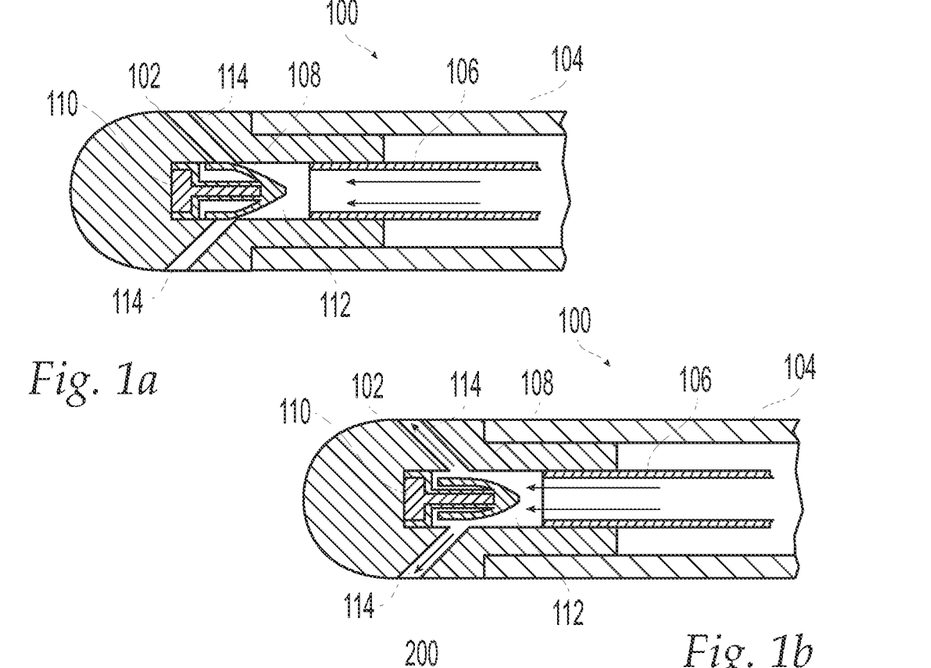
FIG. 1(a) is a cross-sectional view of the distal end of an irrigated ablation catheter with a self-closing valve in the closed position.
FIG. 1(b) is the cross-sectional view of FIG. 1(a) in which the self-closing valve is in the open position.

FIGS. 1(a) and 1(b) are cross-sectional views of the distal end 100 of an irrigated ablation according to one embodiment of the invention. The distal end 100 comprises an electrode 102, a catheter body 104, a fluid tube 106, a valve element 108, and a valve element support core 110. Electrode 102 includes an inner cavity 112 which houses valve element 108 and valve element support core 110, and a plurality of through holes 114 from the inner cavity 112 to the exterior of electrode 102.

Valve element support core 110 may be made of any stiff material and offers structural support to valve element 108. Valve element support core 110 may be attached to electrode 102 and valve element 108 by any means well-known in the art, including, but not limited to bonding and threading. Valve element 110 is in the shape of an umbrella and made of a flexible material such as silicone rubber, polyurethane, and other synthetic rubbers.

Catheter body 104 is a flexible hollow tube attached to the proximal end of electrode 102 by any means well-known in the art such as bonding and swaging. Catheter body 104 may be constructed from a number of different polymers (e.g., PELLETLIANE, polypropylene, oriented polypropylene, polyethylene, crystallized polyethylene terephthalate, polyethylene terephthalate, polyester, polyvinyl chloride, etc.), in which braiding is embedded. Catheter body 104 may be guided by a user by such means well-known in the art as puller wires.

Fluid tube 106 is centered within the catheter body 104, and is attached to the proximal open end of electrode 102 by any means well-known in the art such as bonding or swaging. Fluid tube 106 allows the flow of saline through holes 114 to providing cooling for electrode 102.

The umbrella shape of valve body 110 in the absence of a set amount of pressure, prevents flow of blood into, or saline out of, through holes 114. When the pressure of saline within electrode 102 exceeds a preset amount, valve element 108 collapses around valve element support core 110, allowing passage of the saline through holes 114 to cool electrode 102.

FIG. 1(a) shows distal end 100 with valve element 108 in a position such that it blocks through holes 114, preventing saline flow through holes 114. This is known as the closed position. FIG. 1(b) shows distal end 100 with valve element 108 in a position such that through holes 114 are uncovered, allowing flow through holes 114. This is known as the open position.

While not shown in the figures, signal wires for providing RF energy to the electrode may be routed within the wall of catheter body 104, or in the region between the inner wall of catheter body 104 and the outer diameter of fluid tube 106. The signal wires are preferably electrically insulated from each other to allow the wires to share a single lumen. The signal wires extend the length of catheter body 104. The details of routing of the signal wires are not critical to any embodiment of the present invention.

Figure 2A:
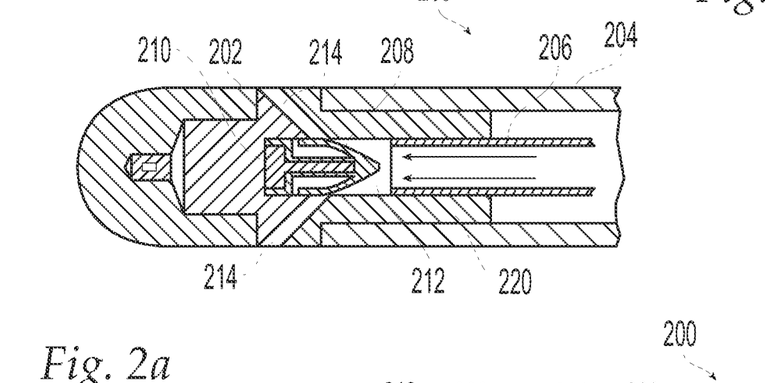
FIG. 2(a) is a cross-sectional view of the distal end of an insulated irrigated ablation catheter with a self-closing valve in the closed position.
Figure 2B:
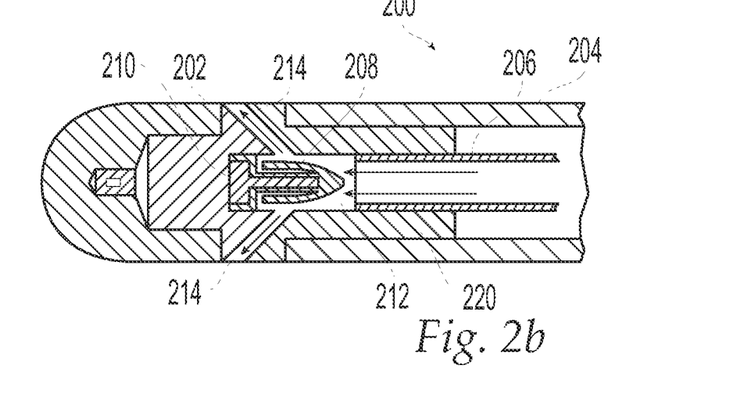
FIG. 2(b) is the cross-sectional view of FIG. 2(a) in which the self-closing valve is in the open position.

FIGS. 2(a) and 2(b) show a modification of the embodiment of the invention shown in FIGS. 1(a) and 1(b), with similar numbers corresponding to the numbers in FIGS. 2(a) and 2(b). The only difference between the invention shown in FIGS. 2(a) and 2(b) and that described above is the presence of a thermally insulating element 220 between electrode 202 and catheter body 204, and that the through holes 214 are in the insulating element 220 rather than in the electrode 202. Thermally insulating element 220 may be made from a plastic such as e.g., DELRIN®, polyetheretherketone (PEEK), and high-density polyethylene (HDPE).

Figure 3A:
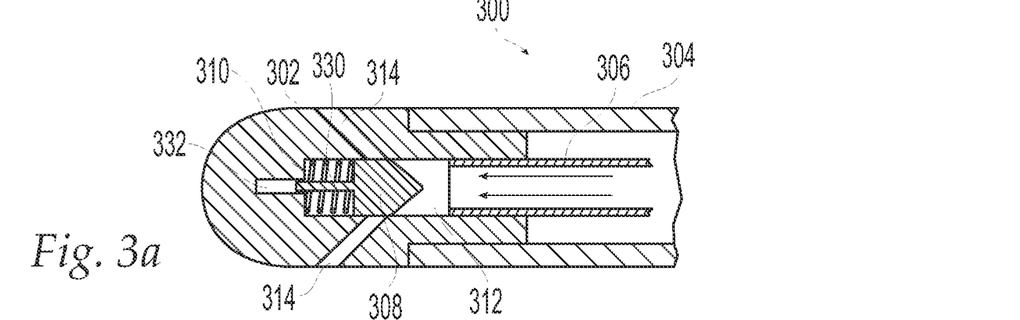
FIG. 3(a) is a cross-sectional view of the electrode at the distal end of the body of an irrigated ablation catheter with a spring-loaded self-closing valve in the closed position.
Figure 3B:
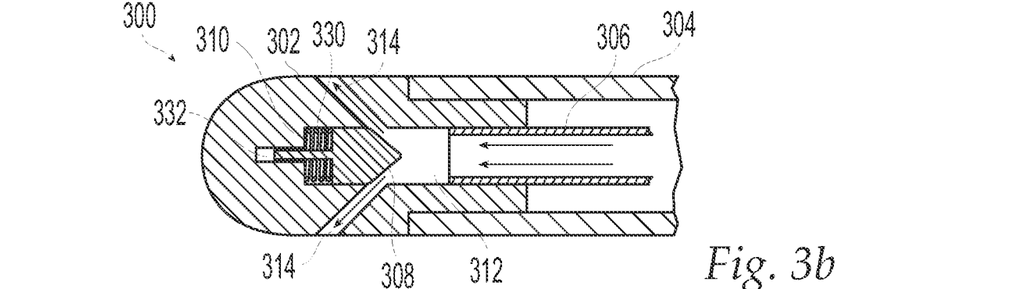
FIG. 3(b) is the cross-sectional view of FIG. 3(a) in which the self-closing valve is in the open position.

FIGS. 3(a) and 3(b) show a cross-sectional view of another embodiment of the invention. The distal end 300 comprises an electrode 302, a catheter body 304, a fluid tube 306, a valve element 308, and a coil spring 310. Electrode 302 includes an inner cavity 312 which houses valve element 308, which has a slightly smaller diameter than the inner diameter of inner cavity 312, and coil spring 310. There is also a plurality of through holes 314 from inner cavity 312 to the outer surface of electrode 302. The distal end of inner cavity 312 includes a reduced diameter extension 332. Stem 330 of valve element 308 has a slightly smaller diameter than reduced diameter extension 332 of inner cavity 312 to allow stem 330 to slide back and forth, so that valve element 308 covers or uncovers through holes 314 to prevent or allow, respectively, saline flow through holes 314. Valve element 308 may be prevented from moving too far in the proximal direction by any number of ways well-known in the art. For example, fluid tube 306 may extend far enough into inner cavity 312 to prevent valve element 308's moving farther in the distal direction, or a reduced diameter section (not shown) of inner cavity 312 may prevent such movement.

Catheter body 304 is a flexible hollow tube attached to the proximal end of electrode 302 by any means well-known in the art such as bonding and swaging. Catheter body 304 may be made of a flexible material such as thermoplastics such as nylon, in which braiding is embedded. Catheter body 304 may be guided by a user by such means well-known in the art as puller wires.

Fluid tube 306 is centered within the catheter body 304, and is attached to the proximal open end of electrode 302 by any means well-known in the art such as bonding or swaging. Fluid tube 306 allows the flow of saline through holes 314 to providing cooling for electrode 302.

Spring coil 310 may be made of any material normally used in producing springs and that is acceptable for use within the human body. Spring coil 310 biases valve element 308 toward a position in which valve element 308 covers through holes 314, preventing flow of saline into a patient's body. If pressure of saline through fluid tube 306, and, consequently, inner cavity 312 exceeds a set amount, valve element 308 is pushed against the biasing force of spring 310 until through holes 314 are uncovered and saline flows into the patient's body.

FIG. 3(*a*) shows distal end 300 with valve element 308 in the closed position. FIG. 3(*b*) shows distal end 300 with valve element 308 in the open position.

Figure 4A:
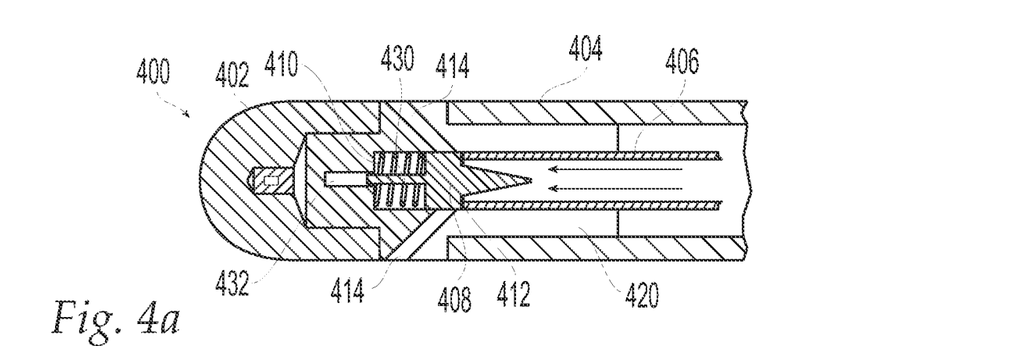
FIG. 4(a) is a cross-sectional view of the electrode at the distal end of the body of an insulated irrigated ablation catheter with a spring-loaded self-closing valve in the closed position.
Figure 4B:
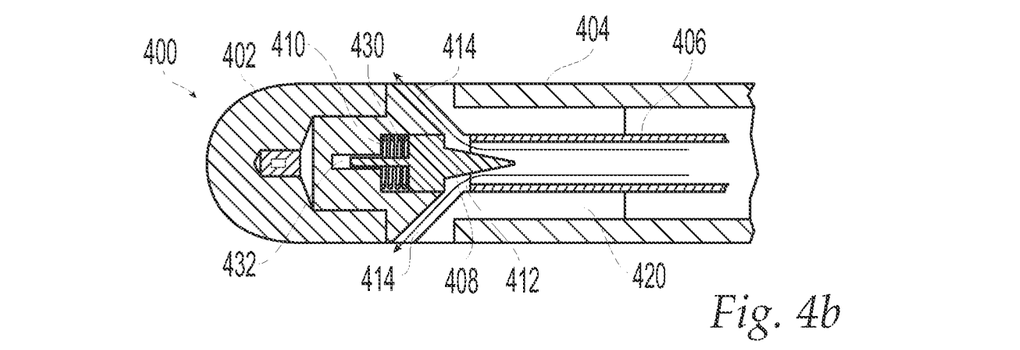
FIG. 4(b) is the cross-sectional view of FIG. 4(a) in which the self-closing valve is in the open position.
Figure 5:
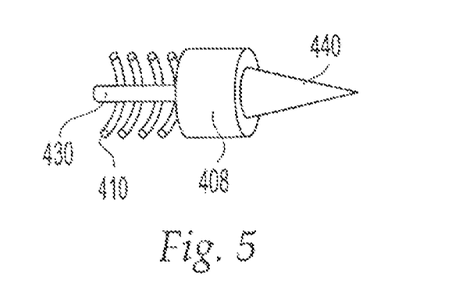
FIG. 5 is a detail of a spring-loaded self-closing valve.

FIGS. 4(*a*) and 4(*b*) show a modification of the embodiment of the invention shown in FIGS. 4(*a*) and 4(*b*), with similar numbers corresponding to the numbers in FIGS. 1(*a*) and 1(*b*). The only difference between the invention shown in FIGS. 4(*a*) and 4(*b*) and that described above with regard to FIGS. 3(*a*) and 3(*b*) is the presence of an insulating element 420 between electrode 402 and catheter body 404, and that the through holes 414 are in the insulating element 420 rather than in the electrode 402. In addition, FIGS. 4(*a*) and 4(*b*) show a conical flow conditioner 440, which reduces turbulent flow, which in turn reduces valve "hunting." FIG. 5 is an isometric view of valve element 408 and coil spring 410. Note that a flow conditioner may also be used with valve element 308 shown in FIGS. 3(*a*) and 3(*b*).

Figure 6A:
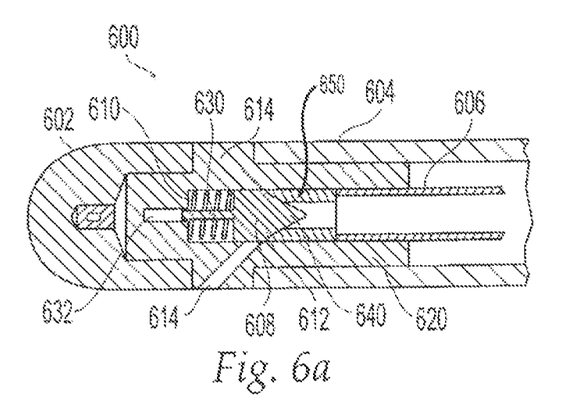
FIG. 6(a) is a cross-sectional view of the electrode at the distal end of the body of an insulated irrigated ablation catheter with a seal member and a spring-loaded self-closing valve in the closed position.
Figure 6B:
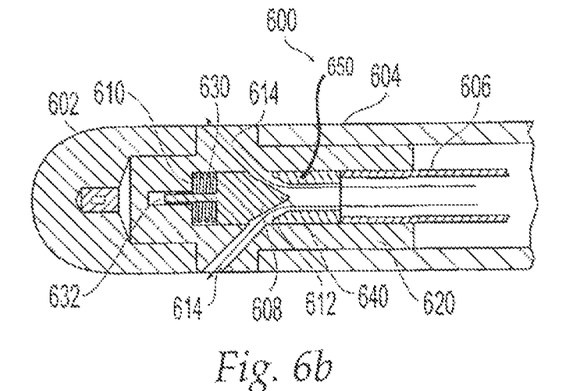
FIG. 6(b) is the cross-sectional view of FIG. 6(a) in which the self-closing valve is in the open position.

FIGS. 6*a* and 6*b* are cross-sectional views of an option available for the embodiments of the invention shown in FIGS. 3-5 with similar numbers corresponding to the numbers in FIGS. 3-5. Seal member 650 is a means of reducing saline leakage through holes 614. Rather than relying solely on the tight clearance between the outer diameter of valve element 608 and the inner diameter of inner cavity 612, seal member 650 provides a sealing surface for the proximal face of valve element 608. Although seal element 650 may be constructed of a rigid material, it is preferably made of an elastomeric material to improve the seal. Seal member 650 also acts as a stop to prevent excessive travel of valve element 608 in the proximal direction. Although shown with an insulated electrode, seal member 650 may also be used in a catheter without an insulated electrode by locating seal member 650 directly inside the electrode.

Figure 7A:
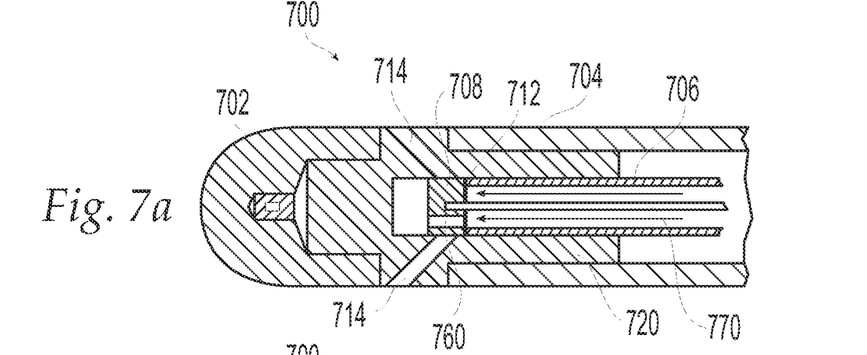
FIG. 7(a) is a cross-sectional view of the distal end of an insulated irrigated ablation catheter with an on/off valve in the closed position actuated by a push/pull wire.
Figure 7B:
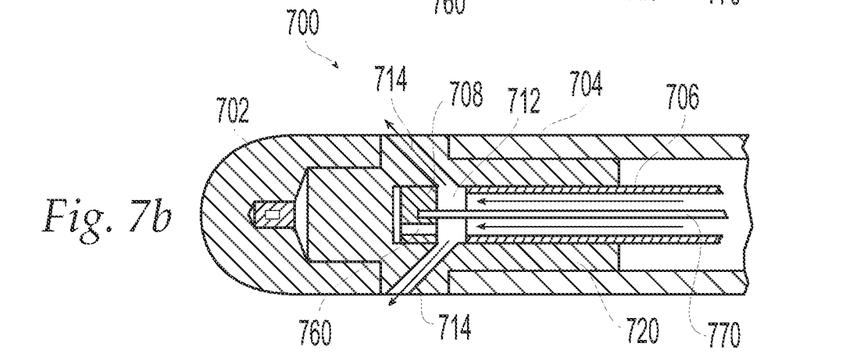
FIG. 7(b) is the cross-sectional view of FIG. 7(a) in which the valve is in the open position.

FIGS. 7(*a*) and 7(*b*) are cross-sectional views of another embodiment of the invention. Rather than using a self-closing valve element as shown in FIGS. 1-6, the embodiment 700 shown in FIGS. 7(*a*) and 7(*b*) relies on a user to open and close the valve.

Valve element 708 is tightly fit into the inner diameter of inner cavity 712 of insulating member 720 (which provides thermal insulation between saline flow and electrode 702) to provide a seal when an operator at the proximal end of catheter body 704 uses push/pull wire 770 to pull valve element 708 toward the proximal end of insulating member 720 to block saline passage through holes 714. Using push/pull wire 770 to push valve element 708 toward the distal end of insulating member 720 to uncover through holes 714 to allow saline to flow. Push/pull wire 770 is made of a flexible material such as stainless steel, titanium, or carbon fiber.

Hole 760 is provided in valve element 708 to allow fluid flow from one side of the other, facilitating movement of valve element 708. If hole 760 is not provided, a suction pocket will form on the distal side of valve element 708 when pulling valve element 708 in the proximal direction. The tight fit between the outer diameter of valve element 708 and the inner diameter of inner cavity 712 would also make it difficult to push valve element 708 into the open position, as it would take more time for saline trapped on the distal side of valve element 708 to flow around the outer diameter of valve element 708 without hole 760.

Valve element 708 may be provided with a flow conditioner as described above. A seal element can also be provided in this embodiment. The method can also be used in an electrode without an insulating element. Rather than being manually operated by a user, push/pull wire 770 can be linked to saline flow such that starting flow will automatically open the valve and stoppage of flow will automatically close the valve. This linkage of operation may be a result of, for example, a double pole/double throw switch actuating push/pull wire 770 in coordination with starting and stopping the saline pump. Alternatively, a flow switch detecting saline flow may be used to actuate push/pull wire 770. In both cases, a limit switch may be used to stop actuation of push/pull wire 770 when the desired valve element position is reached.

Figure 8A:
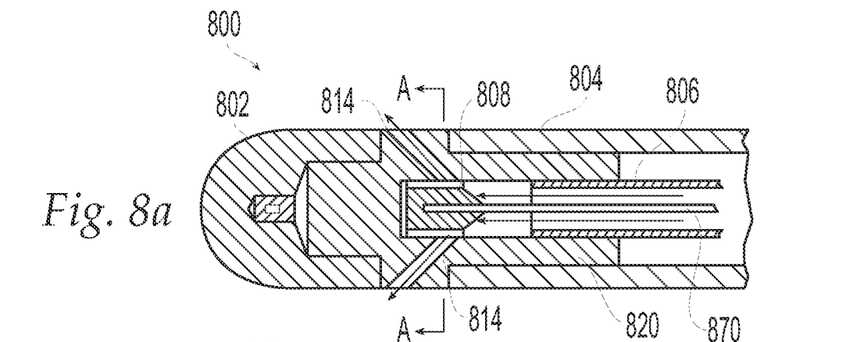
FIG. 8(a) is a cross-sectional view of the distal end of an insulated irrigated ablation catheter with a rotating valve actuated by a rotation wire.

FIG. 8(*a*) is a cross-sectional view of another embodiment (800) of the invention. As with the embodiment shown in FIGS. 7(*a*) and 7(*b*), this embodiment relies on a user to open and close the valve rather than using a self-closing valve element.

Figure 8B:
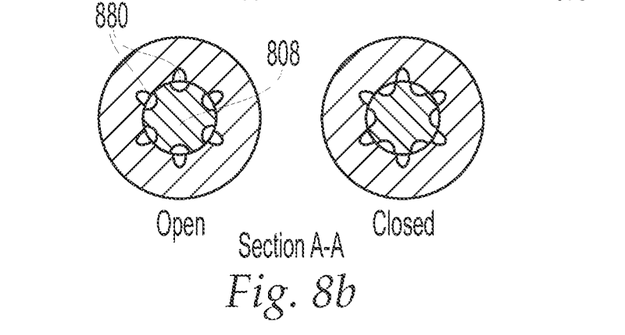
FIG. 8(b) is section A-A of the cross-sectional view of FIG. 8(a) in both the open and closed positions.

FIG. 8(*b*) is section A-A taken through insulating element 820 and valve element 808 showing both open and closed positions of valve element 808. Valve element 808 includes scalloped portions 880 and is tightly fit into the inner diameter of insulating member 820 (which provides thermal insulation between saline flow and electrode 802). A user at the proximal end of catheter body 804 rotates rotation wire 870 to place valve element 808 in the open position when scalloped portions 880 align with through holes 814 and in the closed position when scalloped portions 880 do not align with through holes 814. Rotation wire 870 is made of a flexible material such as stainless steel, titanium, or carbon fiber.

As with the embodiment shown in FIGS. 7(*a*) and 7(*b*), valve element 808 may be provided with a flow conditioner as described above. A seal element can also be provided in this embodiment. The method can also be used in an electrode without an insulating element. Rather than being manually operated by a user, rotation wire 870 can be linked to saline flow such that starting flow will automatically open the valve and stoppage of flow will automatically stop flow. This linkage of operation may be a result of, for example, a double pole/double throw switch actuating rotation wire 870 in coordination with starting and stopping the saline pump. Alternatively, a flow switch detecting saline flow may be used to actuate rotation wire 870. In both cases, a limit switch may be used to stop actuation of rotation wire 870 when the desired valve element position is reached.

Figure 9A:
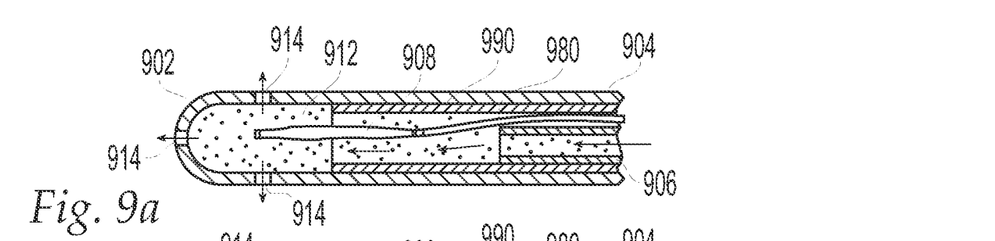
FIG. 9(a) is a cross-sectional view of the distal end of an irrigated ablation catheter with an on/off valve comprising a balloon in the on (deflated) position.
Figure 9B:
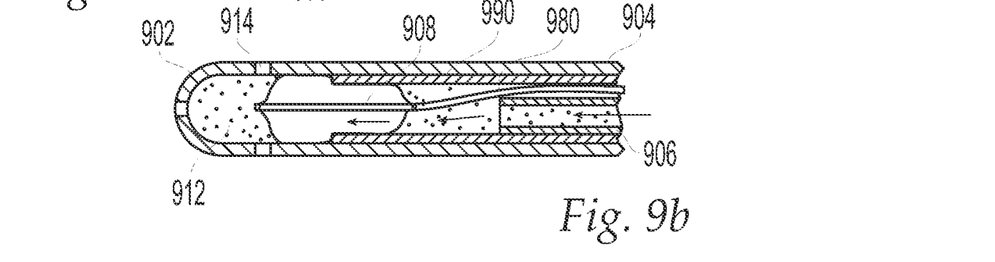
FIG. 9(b) is the sectional view of FIG. 9(a) with the balloon in the off (inflated) position.

FIGS. 9(*a*) and 9(*b*) are cross-sectional views of yet another embodiment of the invention. In this embodiment balloon 908 inflates to fill inner cavity 912 to prevent flow through holes 914 and deflates to allow flow through holes 914. The fluid to inflate balloon 908 is admitted and released through inflation tube 980. A syringe pump at the distal end of catheter body 904 controls the admission and release of fluid through inflation tube 980. As shown, inflation tube 980 passes through a bushing 990 located between the outer diameter of fluid tube 906 and the inner diameter of inner cavity 912. However, inflation tube may also be located inside fluid tube 906.

The method can also be used in an electrode without an insulating element. Rather than being manually operated by a user, operation of the syringe pump can be linked to saline flow such that starting flow will automatically inflate the balloon and stoppage of flow will automatically deflate the balloon. This linkage of operation may be a result of, for example, a double pole/double throw switch actuating the syringe pump in coordination with starting and stopping the saline pump. Alternatively, a flow switch detecting saline flow may be used to actuate the syringe pump. In both cases, a pressure switch may be used to stop actuation of the syringe pump when the desired balloon inflation or deflation is reached.

Figure 10B:
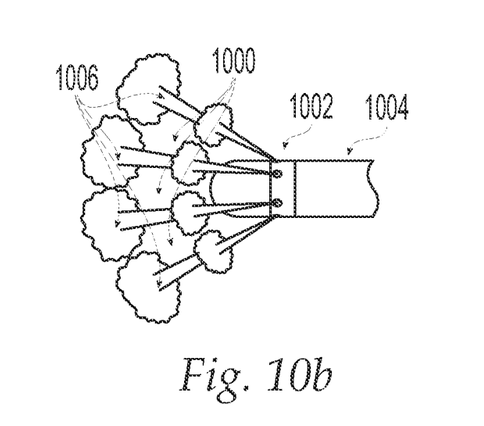
FIG. 10(b) is an illustration of pulsatile irrigation flow.

The embodiments shown in FIGS. 1(*a*)-9(*b*) also lend themselves to producing pulsatile flow as shown in FIGS. 10(*b*) and 11(*b*). As generally illustrated in FIG. 11(*b*), the pulsatile flow is characterized by a flow rate of a particular amount (e.g., 20 ml/minute) that recurs at regular intervals over time.

Figures 11A, 11B:
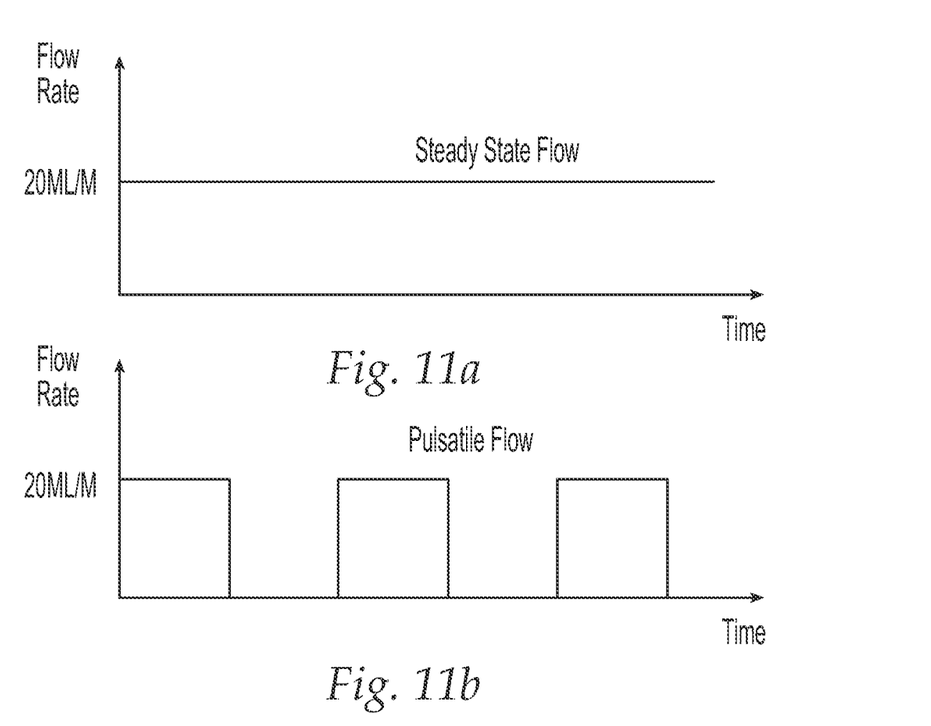
FIG. 11(a) is a flow chart of steady state flow.
FIG. 11(b) is a flow chart of pulsatile flow.

FIG. 10(*a*) shows stagnation area 1000 at the distal end of electrode 1002 when a catheter 1004 contacts the tissue in parallel with the tissue surface and saline flow 1006 is used for cooling at, e.g., the steady state flow rate shown in FIG. 11(*a*). FIG. 10(*b*) shows a reduction in stagnant areas as a result of pulsatile cooling flow at, e.g., the intermittent flowrates shown in FIG. 11(*b*) in which a particular flow rate recurs at regular intervals over time. FIGS. 13(*a*)-(*d*) are photographs of flow using a die with both steady state and pulsatile flow. FIGS. 13(*a*) and 13(*c*) show steady state flow in an external irrigated catheter and an open irrigated catheter, respectively. FIGS. 13(*b*) and 13(*c*) show pulsatile flow in an external irrigated catheter and an open irrigated catheter, respectively. FIGS. 13(*b*) and 13(*c*) clearly show a dramatic reduction in stagnant areas despite a 50% drop in total saline flow. Alternatively, the total flow could remain the same with pulsatile flow as with steady state flow.

Pulsatile flow can be created using a stepper motor with a positive displacement pump. In that case, a valve as shown in one of FIGS. 1(*a*)-9(*b*) is not required for producing pulsatile flow, but assists in preventing backflow of blood into the electrode. Alternatively, pulsatile flow can be created using an on/off valve, an expandable compliance chamber, and a pump.

Figure 14:
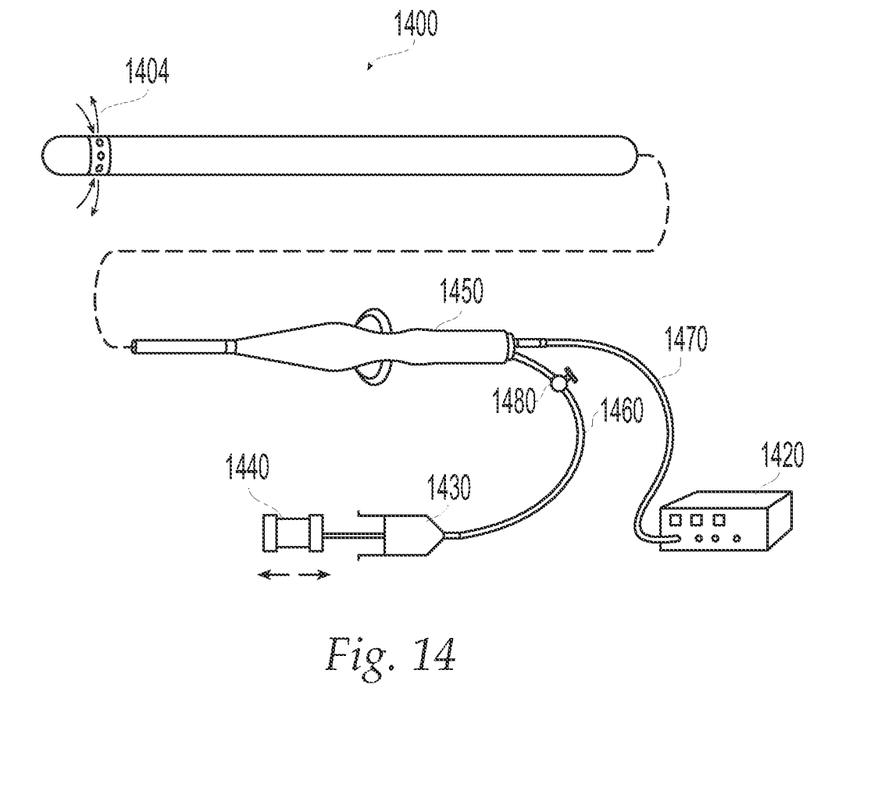
FIG. 14 is a depiction of an RF ablation system using pulsatile flow using a conventional irrigated ablation catheter.

FIG. 14 shows a complete catheter set-up using a pump with a stepping motor to create pulsatile flow. The set-up comprises catheter 1400 with electrode 1404, RF generator 1420, syringe pump 1430, stepper motor 1440, proximal end control handle 1450, tubing 1460, RF generator leads 1470, and valve 1480.

A user maneuvers the distal end (end with electrode 1404) by manipulating proximal end control handle 1450 by any means well-known in the art including, but not limited to, pull wires When electrode 1404 is in the proper location, the user activates RF generator 1420 and stepper motor 1440 to generate pulsatile flow. The RF generator provides a signal through RF generator leads to electrode 1404 to allow electrode 1404 to perform ablation. Valve 1480 may be used to stop fluid flow to the catheter. Anticoagulant drugs may also be administered by a separate pump and tube leading to the region of the lumen of catheter 1400 adjacent to electrode 1404 (i.e., on the electrode side of the piston, pump, or bushing).

Figure 12:
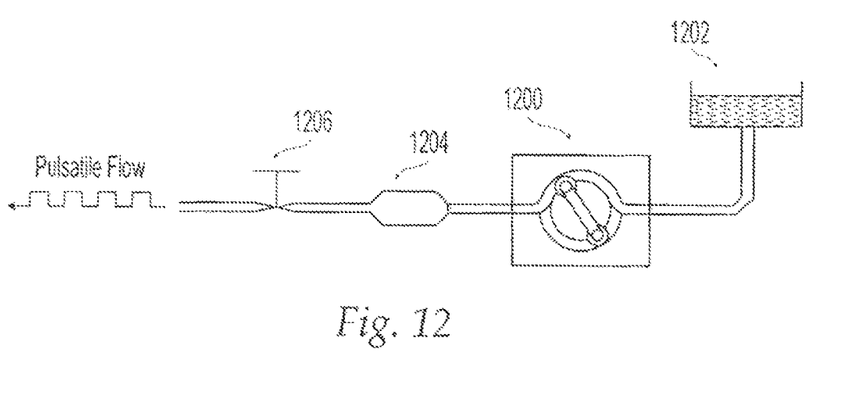
FIG. 12 is a diagram of an alternative method of generating pulsatile flow.

FIG. 12 shows an alternative method of creating pulsatile flow. Peristaltic tubing pump 1200 pumps saline from reservoir 1202 sequentially through compliance chamber 1204 and on/off valve 1206. Pulsatile chamber 1204 is expandable to allow it to absorb flow when on/off valve 1206 is in the "off" position. Valve 1206 alternates between the on and off positions to intermittently allow flow.

While 1200 is shown as a peristaltic tubing pump, it may be any type of pump normally used for saline irrigation of catheters.

Valve 1206 may be a valve such as shown in FIGS. 7(*a*) and 7(*b*), or FIGS. 8(*a*) and 8(*b*). It may also be a ball valve, gate valve, diaphragm valve, globe valve, butterfly valve or any other valve well-known in the art. Valve 1206 may be operated by a solenoid, a motor, pneumatics, hydraulics, or any other non-manual means of control well-known in the art.

Valve 1206 may be located near the distal tip of the catheter as with valve elements 708 and 808 in FIGS. 7(*a*) and 7(*b*), and 8(*a*) and 8(*b*), respectively. It may also be located in a proximal handle of the catheter. If valve 1206 is located in the proximal handle of the catheter, a valve as shown in one of FIGS. 1(*a*)-9(*b*) is not required for producing pulsatile flow, but will assist in preventing blood flow into the electrode.

Compliance chamber 1204 may be constructed of an elastic tube made of polyurethane, silicone, or any other elastic material suitable for such purposes in a medical setting. Compliance chamber 1204 may be located in a proximal handle of the catheter or between pump 1200 and a proximal handle of the catheter.

Both external irrigated ablation catheters and open irrigated catheters can benefit from pulsatile irrigation flow. External irrigation flow refers to irrigation flow coming from components of a catheter other than the electrode to cool the electrode externally. Open irrigation flow refers to irrigation flow coming from inside an electrode to outside the electrode. Most irrigated ablation catheters currently available are of the open irrigated type.

Although the embodiments of this invention have been described above with a certain degree of particularity, those skilled in the art could make numerous alterations to the disclosed embodiments without departing from the spirit or scope of this invention. For example, any means of causing a reciprocating flow could be used. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An irrigated ablation catheter system comprising:
an irrigated ablation catheter; and
a pump system configured to generate a variable flow of a fluid, wherein
the irrigated ablation catheter comprises a distal electrode assembly, a shaft connected to the distal electrode assembly, and an interior portion leading to one or more openings through which the variable flow of the fluid is directed from within the irrigated ablation catheter to an area outside the irrigated ablation catheter, and wherein the variable flow is characterized by a flow rate that varies at intervals over time with a frequency less than 120 cycles per minute.

2. The irrigated ablation catheter system of claim 1, wherein the irrigated ablation catheter further includes a valve movable between a first position to block the variable flow of the fluid through the one or more openings and a second position to unblock variable flow through the one or more openings.

3. The irrigated ablation catheter system of claim 1, wherein the valve is moved between the first position and the second position in response to a variable pressure generated by the pump system in an interior portion of the irrigated ablation catheter.

4. The irrigated ablation catheter system of claim 1, wherein the irrigated ablation catheter is configured to direct the fluid to an external portion of the distal electrode assembly.

5. The irrigated ablation catheter system of claim 1, wherein the distal electrode assembly is configured to direct the fluid to an external portion of the distal electrode assembly.

6. The irrigated ablation catheter system of claim 1, wherein the pump system comprises a positive displacement pump driven by a stepper motor.

7. The irrigated ablation catheter system of claim 1, wherein the flow rate is between 2 ml/minute and 20 ml/minute with the frequency of between 30 cycles per minute to 120 cycles per minute.

8. The irrigated ablation catheter system of claim 1, wherein the pump system is configured to generate the variable flow by an on/off valve, wherein the on/off valve is configured to have an on position which unblocks the one or more openings, a compliance chamber, and a positive displacement pump.

9. The irrigated ablation catheter system of claim 8, wherein the on/off valve and the compliance chamber are located inside the shaft of the irrigated ablation catheter.

10. The irrigated ablation catheter system of claim 8, wherein the on/off valve is a push/pull type valve to cover and uncover the one or more openings to prevent and allow the variable flow.

11. The irrigated ablation catheter system of claim 1, further comprising an insulating element that provides thermal insulation between the one or more openings for fluid flow and the distal electrode assembly.

12. The irrigated ablation catheter system of claim 1, further comprising a valve to prevent backflow of fluids into the catheter.

13. The irrigated ablation catheter system of claim 12, wherein the valve to prevent backflow of fluids into the catheter is umbrella-shaped, and collapsible and expandable to uncover and cover the one or more openings to allow and prevent the variable flow.

14. The irrigated ablation catheter system of claim 1, wherein the variable flow comprises a pulsatile flow.

15. The irrigated ablation catheter system of claim 1, wherein the intervals at which the flow rate varies comprise regular intervals.

16. An irrigated ablation catheter comprising:
an electrode assembly having an inner cavity and a plurality of irrigation holes;
an elongate shaft;
a proximal handle;
a fluid lumen having a distal end and a proximal end, the distal end connecting to the proximal handle;
an on/off valve located inside of the proximal handle to control passage of a fluid;
a volume compliance chamber having an expandable body, a distal end, and proximal end,
wherein the distal end of the volume compliance chamber connects to the on/off valve and the proximal end of the volume compliance chamber connects to the fluid lumen, the volume compliance chamber is located within the proximal handle, wherein the volume compliance chamber is configured to expand when the on/off valve is in an off position, and an on position of the on/off valve unblocks the plurality of irrigation holes, and wherein a frequency that the volume compliance chamber cycles is less than 120 times per minute.

17. The irrigated ablation catheter of claim 16, wherein the on/off valve is controlled by an electronic circuit permitting variations in on and off durations and frequencies.

18. The irrigated ablation catheter of claim 16, wherein the on and off durations are 50% and 50%, respectively.

19. The irrigated ablation catheter of claim 16, wherein the on and off durations are variable between 30% and 70%.

20. An irrigated ablation catheter system comprising:
an irrigated ablation catheter comprising a distal electrode assembly, a shaft connected to the distal electrode assembly, and an interior portion leading to one or more openings; and
a pump system configured to generate a variable flow,
wherein the variable flow is configured to flow through the one or more openings to an area external the distal electrode assembly, wherein the variable flow is characterized by a flow rate that varies at intervals over time with a frequency less than 120 cycles per minute.

21. The irrigated ablation catheter system of claim 20, wherein a flow rate of the variable flow is between 2 ml/minute and 20 ml/minute with a frequency of between 30 cycles per minute to 120 cycles per minute.

22. The irrigated ablation catheter system of claim 20, wherein the irrigated ablation catheter further comprises a valve to prevent backflow of fluids into the distal electrode assembly.

* * * * *